United States Patent
Böttcher et al.

(10) Patent No.: US 7,388,119 B2
(45) Date of Patent: Jun. 17, 2008

(54) METHOD FOR THE HYDROGENATION OF AROMATIC COMPOUNDS WITH HYDROGEN CONTAINING RESIDUAL GAS

(75) Inventors: Arnd Böttcher, Frankenthal (DE); Ekkehard Schwab, Neustadt (DE); Ralf Kästner, Alzey (DE); Jochem Henkelmann, Mannheim (DE); Gerd Kaibel, Lampertheim (DE); Heinrich Laib, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 803 days.

(21) Appl. No.: 10/484,247

(22) PCT Filed: Jul. 18, 2002

(86) PCT No.: PCT/EP02/08023

§ 371 (c)(1),
(2), (4) Date: Jan. 20, 2004

(87) PCT Pub. No.: WO03/010119

PCT Pub. Date: Feb. 6, 2003

(65) Prior Publication Data

US 2004/0215042 A1    Oct. 28, 2004

(30) Foreign Application Priority Data

Jul. 20, 2001    (DE) ................. 101 35 490

(51) Int. Cl.
*C07C 5/10*    (2006.01)
(52) U.S. Cl. .............. 585/379; 585/380; 585/317
(58) Field of Classification Search ............... 585/379, 585/380, 317
See application file for complete search history.

(56) References Cited

U.S. PATENT DOCUMENTS

| | | | | |
|---|---|---|---|---|
| 2,898,387 A | 8/1959 | Teter | ........ | 260/667 |
| 3,054,833 A | 9/1962 | Donaldson et al. | ........ | 260/667 |
| 3,202,723 A | 8/1965 | Thonon | ........ | 260/667 |
| 3,202,733 A | 8/1965 | Strauss | ........ | 260/49 |
| 3,244,644 A | 4/1966 | Stiles | ........ | 252/466 |
| 3,597,489 A | 8/1971 | Vu et al. | ........ | 260/667 |
| 3,917,540 A | 11/1975 | Pollitzer | ........ | 252/466 |
| 4,067,915 A | 1/1978 | Yasuhara et al. | ........ | 260/648 |
| 5,668,293 A | 9/1997 | Forestiere et al. | ........ | 585/269 |
| 6,255,530 B1 | 7/2001 | Albach et al. | ........ | 564/450 |

FOREIGN PATENT DOCUMENTS

| | | |
|---|---|---|
| DE | 199 17 051 | 10/2000 |
| DE | 100 50 711 | 4/2002 |
| DE | 101 28 242 | 10/2002 |
| DE | 101 50 709 | 4/2003 |
| EP | 668 257 | 8/1995 |
| GB | 799396 | 8/1958 |
| GB | 1039381 | 8/1966 |
| GB | 1104275 | 2/1968 |
| GB | 1144499 | 3/1969 |
| GB | 1155539 | 6/1969 |
| GB | 1341057 | 12/1973 |
| SU | 319582 | 5/1970 |
| SU | 403658 | 1/1972 |
| WO | WO 01/10802 | 2/2001 |

*Primary Examiner*—Thuan Dinh Dang
(74) *Attorney, Agent, or Firm*—Novak Druce + Quigg LLP

(57) ABSTRACT

The present invention relates to a process for the hydrogenation of substituted or unsubstituted, monocyclic or polycyclicaromatics to form the corresponding cycloaliphatics, in particular of benzene to cyclohexane, by bringing the aromatic into contact with a hydrogen-containing gas in the presence of a catalyst, where hydrogen in which residual gases are present is used.

11 Claims, No Drawings

METHOD FOR THE HYDROGENATION OF AROMATIC COMPOUNDS WITH HYDROGEN CONTAINING RESIDUAL GAS

The present invention relates to a process for the hydrogenation of substituted or unsubstituted, in particular alkyl-substituted, monocyclic or polycyclic aromatics to form the corresponding cycloaliphatics, in particular of benzene to form cyclohexane, by bringing the aromatic into contact with a hydrogen-containing gas in the presence of a catalyst, wherein hydrogen in which residual gases are present is used.

There are numerous processes for the hydrogenation of benzene to cyclohexane. These hydrogenations are predominantly carried out in the gas phase or the liquid phase over nickel and platinum catalysts (cf., inter alia, U.S. Pat. No. 3,597,489, U.S. Pat. No. 2,898,387 and GB 799 396). Typically, the major part of the benzene is firstly hydrogenated to cyclohexane in a main reactor and the conversion to cyclohexane is subsequently completed in one or more after-reactors.

The strongly exothermic hydrogenation reaction requires careful temperature and residence time control in order to achieve complete conversion at high selectivity. In particular, significant formation of methylcyclopentane, which proceeds preferentially at relatively high temperatures, has to be suppressed. Typical cyclohexane specifications require a residual benzene content of <100 ppm and a methylcyclopentane content of <200 ppm. The content of n-paraffins (n-hexane, n-pentane, etc) is also critical. These undesirable compounds are likewise preferentially formed at relatively high hydrogenation temperatures and can, like methylcyclopentane, be separated from the cyclohexane produced only by means of complicated separation operations (extraction, rectification or, as described in GB 1 341 057, use of molecular sieves). The catalyst used for the hydrogenation also has a strong influence on the extent to which the undesirable methylcyclohexane is formed.

In view of this background, it is desirable to carry out the hydrogenation at the lowest possible temperatures. However, this is limited by the fact that, depending on the type of hydrogenation catalyst used, a catalyst activity sufficient to obtain economically acceptable space-time yields in the hydrogenation is reached only above relatively high temperatures.

The nickel and platinum catalysts used for the hydrogenation of benzene have a series of disadvantages. Nickel catalysts are very sensitive to sulfur-containing impurities in the benzene, so that it is necessary either to use very pure benzene for the hydrogenation or, as described in GB 1 104 275, to use a platinum catalyst which tolerates a relatively high sulfur content in the main reactor and thus protect the after-reactor which is charged with a nickel catalyst. Another possibility is doping the catalyst with rhenium (GB 1 155 539) or preparing the catalyst for using ion exchangers (GB 1 144 499). However, the production of such catalysts is complicated and expensive. The hydrogenation can also be carried out over Raney nickel (U.S. Pat. No. 3,202,723), but a disadvantage is the fact that this catalyst is readily combustible. Homogeneous nickel catalysts can also be used for the hydrogenation (EP A 0 668 257). However, these catalysts are very sensitive to water so that the benzene used has to be dried to a residual water content of <1 ppm in a drying column prior to the hydrogenation. A further disadvantage of the homogeneous catalyst is that it cannot be regenerated.

WO 01/10802 describes a process for preparing cyclohexane by hydrogenation of benzene, in which the hydrogen source can contain impurities. The catalyst used for the process described there comprises nickel and copper and optionally further metals. However, the nickel and copper catalysts used there have the disadvantage that they have to be prereduced prior to the actual hydrogenation.

Platinum catalysts have fewer disadvantages than nickel catalysts, but are much more expensive to produce. The use of both platinum and nickel catalysts requires very high hydrogenation temperatures, which can lead to significant formation of undesirable by-products.

References to the use of ruthenium-containing catalysts for this application may also be found in the patent literature:

In SU 319582, suspended Ru catalysts doped with Pd, Pt or Rh are used for preparing cyclohexane from benzene. However, the use of Pd, Pt or Rh makes the catalysts very expensive. Furthermore, the work-up and recovery of the catalyst is complicated and expensive in the case of suspended catalysts.

In SU 403658, a Cr-doped Ru catalyst is used for preparing cyclohexane. However, the hydrogenation is carried out at 180° C. and a significant amount of undesirable by-product is generated.

U.S. Pat. No. 3,917,540 claims $Al_2O_3$-supported catalysts for preparing cyclohexane. These comprise, as active metal, a noble metal of transition group VIII of the Periodic Table together with an alkali metal and also technetium or rhenium. The hydrogenation of benzene can be carried out over such catalysts, but in a selectivity of only 99.5%.

U.S. Pat. No. 3,244,644 describes ruthenium hydrogenation catalysts supported on $\eta$-$Al_2O_3$, and these are set to be suitable, inter alia, for the hydrogenation of benzene. However, the catalysts contain at least 5% of active metal, and the preparation of $\eta$-$Al_2O_3$ is complicated and expensive.

DE 100 50 711.5 describes a process for hydrogenation by means of reactive distillation in a reaction column in which the reactants are conveyed in countercurrent over the catalyst fixed in the reaction column. PCT/EP 00/03326 describes a process for the hydrogenation of substituted or unsubstituted aromatics in the presence of a catalyst comprising at least one metal of transition group VIII of the Periodic Table as active metal applied to a macroporous support. A process for the hydrogenation of aromatics in the presence of a catalyst comprising an active metal of transition group VIII of the Periodic Table on a monolithic support is described in DE 101 50 709.3. DE 101 282 42.7 relates to a process for the hydrogenation of organic compounds, in particular aromatic compounds, in which the catalyst comprises ruthenium as active metal on a silicon dioxide support. In the processes mentioned in these applications, the hydrogenation is carried out by bringing a hydrogen-containing gas into contact with the aromatic, where gases which can be used are any gases which comprise free hydrogen and contain no harmful amounts of catalyst poisons. In particular, pure hydrogen is used as hydrogenation gas.

It is an object of the present invention to provide a process for the hydrogenation of substituted or unsubstituted, monocyclic or polycyclic aromatics to form the corresponding cycloaliphatics, in particular of benzene to give cyclohexane, which process makes it possible to obtain the cycloaliphatic with very high selectivity and in a high space-time yield from inexpensive starting materials.

We have found that this object is achieved by a process for the hydrogenation of at least one substituted or unsubstituted, monocyclic or polycyclic aromatic by bringing the aromatic or aromatics into contact with a hydrogen-containing gas in the presence of a catalyst which comprises at least one metal of transition group VIII of the Periodic Table as active metal, wherein hydrogen in which residual gases are present is used.

The use of hydrogen in which residual gases are present enables a purification step for the starting materials, which leads to increased costs, to be saved in the process of the present invention. According to the present invention, it is also possible, for example, to use hydrogen which is obtained as by-product in another process and in which residual gases are present. In this way, the process of the present invention can be carried out particularly inexpensively.

For the purposes of the present invention, residual gases are, for example, carbon monoxide, carbon dioxide, water, methane or C2-C7-hydrocarbons. The hydrogen in which residual gases are present used according to the present invention may also contain mixtures of two or more thereof. Apart from the abovementioned residual gases, it is also possible for small amounts of, for example, oxygen, ethane, benzene, toluene, ethylbenzene or styrene or volatile or low-boiling sulfur-containing compounds, e.g. hydrogen sulfide or thiophenes, to be present in the hydrogen in which residual gases are present.

The present invention accordingly provides, in a further embodiment, a process in which the hydrogen in which residual gases are present comprises carbon monoxide, carbon dioxide, water, methane or C2-C7-hydrocarbons or mixtures of two or more thereof.

The proportion of residual gases in the hydrogenation gas used is, according to the present invention, at least 2% by volume, in particular more than 5% by volume, preferably at least 10% by volume, in particular at least 15% by volume, in each case based on the sum of hydrogen and residual gases.

The invention therefore provides, in a further embodiment, a process in which the hydrogen in which residual gases are present contains at least 2% by volume, for example at least 5% by volume, preferably at least 10% by volume, in particular at least 15% by volume, of residual gases selected from the group consisting of carbon monoxide, carbon dioxide, water, methane and $C_2$-$C_7$-hydrocarbons.

According to the present invention, the hydrogen in which residual gases are present used as hydrogenation gas can have, for example, the following composition, from 50 to 98% by volume of $H_2$, <5% by volume of CO, from 0.01 to 15% by volume of $CO_2$, from 0 to 2% by volume of water, from 0 to 5% by volume of $N_2$, from 0 to 5% by volume of other aromatics or aliphatic hydrocarbons, preferably <75% by volume of $H_2$, from 0.01 to 5% by volume of CO, from 0.2 to 10% by volume of $CO_2$, from 0 to 1% by volume of water, from 0 to 5% by volume of $N_2$, from 0 to 3% by volume of other aromatic or aliphatic hydrocarbons, in particular hydrocarbons having from 3 to 7 carbon atoms. The percentages by volume are based on the sum of the constituents of the hydrogen in which residual gases are present. Apart from those mentioned above, further constituents such as ethane, benzene, ethylbenzene or styrene can also be present, in particular when the hydrogen in which residual gases are present has been obtained in the dehydrogenation of styrene.

Hydrogen in which residual gases are present and which is suitable for the hydrogenation process of the present invention is obtained, for example, in the industrial dehydrogenation of ethylbenzene to styrene or of propane to propene.

The invention accordingly provides, in a preferred embodiment, a process which is carried out using hydrogen in which residual gases are present and which is obtained in the dehydrogenation of ethylbenzene to styrene or of propane to propene.

The dehydrogenation of propane to propene can be, for example, a process described by Trifirò, Cavani in Katalytica Stud. 4192 OD "Oxidative Dehydrogenation and alternative Dehydrogenation Processes".

This method of carrying out the process is particularly advantageous since hydrogen in which residual gases are present is obtained in large quantities in the dehydrogenation and can in this way be utilized further without costly purification steps being necessary. The reuse of a by-product of the industrial production of styrene or propene leads to a particularly effective process which not only utilizes a by-product but at the same time minimizes environmental pollution.

It has surprisingly been found that the residual gases present according to the present invention in the hydrogen do not affect the selectivity and activity of the catalyst. The substituted or unsubstituted aromatics can be hydrogenated selectively and in a high space-time yield at low temperatures to form the corresponding cycloaliphatics. The product quality does not suffer either. At the low temperatures which can be used according to the present invention, there is virtually no formation of undesirable by-products such as methylcyclopentane or other n-paraffins, so that complicated purification of the cycloaliphatics produced becomes unnecessary.

The catalyst used for the process of the present invention comprises at least one metal of transition group VIII of the Periodic Table as active metal. The catalyst can, for example, comprise, as active metal, a metal of transition group VIII of the Periodic Table, either alone or together with at least one metal of transition group I, VII or VIII of the Periodic Table. The active metal is preferably at least one metal selected from the group consisting of ruthenium, palladium and rhodium. Particular preference is given to ruthenium as active metal.

The active metal can, according to the present invention, be applied to a support. In one embodiment, the process of the present invention is carried out using a catalyst comprising at least one metal of transition group VIII of the Periodic Table as active metal applied to a macroporous support.

The present invention therefore provides, in one embodiment, a process for the hydrogenation of at least one substituted or unsubstituted, monocyclic or polycyclic aromatic using a catalyst which comprises at least one metal of transition group VIII of the Periodic Table as active metal applied to a macroporous support.

As support, it is in principle possible to use all supports in which macropores are present, i.e. either supports which contain exclusively macropores or supports containing both macropores and mesopores and/or micropores.

As active metal, it is possible to use metals of transition group VIII of the Periodic Table either alone or together with a metal of transition group I, VII or VIII of the Periodic Table, preferably ruthenium, palladium or rhodium or mixtures of two or more thereof. Particular preference is given to using ruthenium as active metal. Among the metals of transition groups I, VII and VIII of the Periodic Table which can likewise all be used in principle, preference is given to using copper and/or rhenium.

The terms "macropores" and "mesopores" are used for the purposes of the present invention as they are defined in Pure Appl. Chem., 45, p. 79 (1976), namely as pores whose diameter is above 50 nm (macropores) or whose diameter is in the range from 2 nm to 50 nm (mesopores). "Micropores" are likewise defined as in the above reference and are pores having a diameter of <2 nm.

In a preferred embodiment, the present invention provides a process of this type in which the catalyst comprises, as active metal, at least one metal of transition group VIII of the Periodic Table either alone or together with at least one metal of transition group I, VII or VIII of the Periodic Table applied to a support, where the support has a mean pore diameter of at least 50 nm and a BET surface area of not more than 30 $m^2/g$ and the amount of active metal is from 0.01 to 30% by weight, based on the total weight of the catalyst (catalyst 1). The mean pore diameter of the support in this catalyst is more preferably at least 0.1 µm and the BET surface area is not more than 15 $m^2/g$ (catalyst 1a).

The invention further provides a process of this type in which the catalyst comprises, as active metal, at least one metal of transition group VIII of the Periodic Table either alone or together with at least one metal of transition group I, VII or VIII of the Periodic Table in an amount of from 0.01 to 30% by weight, based on the total weight of the catalyst, applied to a support, where from 10 to 50% of the pore volume of the support is made up by macropores having a pore diameter in the range from 50 nm to 10,000 nm and from 50 to 90% of the pore volume of the support is made up by mesopores having a pore diameter in the range from 2 to 50 nm, where the sum of the pore volumes is 100% (catalyst 2).

The active metal content is generally from about 0.01 to about 30% by weight, preferably from about 0.01 to about 5% by weight and in particular from about 0.1 to about 5% by weight, in each case based on the total weight of the catalyst used. The contents used in the preferred catalysts 1 and 2 described below are indicated again individually in the discussion of these catalysts.

The catalysts 1 and 2 which are preferably used will now be described in detail below. The description is based by way of example on the use of ruthenium as active metal, but the details given are also applicable to the other active metals which can be used, as defined herein.

Catalyst 1

The catalysts 1 used according to the present invention can be produced industrially by applying at least one metal of transition group VIII of the Periodic Table and, if desired, at least one metal of transition groups I, VII or VIII of the Periodic Table to a suitable support.

The application to the support can be achieved by steeping the support in aqueous metal salt solutions, e.g. aqueous ruthenium salt solutions, by spraying appropriate metal salt solutions onto the support or by other suitable methods. Suitable metal salts of metals of transition groups I, VII and VIII of the Periodic Table are the nitrates, nitrosyl nitrates, halides, carbonates, carboxylates, acetylacetonates, chloro complexes, nitrito complexes or amine complexes of the corresponding metals, with preference being given to the nitrates and nitrosyl nitrates.

In the case of catalysts which comprise not only the metal of transition group VIII of the Periodic Table but also further metals as active metal on the support, the metal salts or metal salt solutions can be applied simultaneously or in succession.

The supports which have been coated or impregnated with the metal salt solution are subsequently dried, preferably at from 100 to 150° C., and, if desired, calcined at from 200 to 600° C., preferably from 350 to 450° C. In the case of stepwise application, the catalyst is dried and, if appropriate, calcined after each impregnation step, as described above. The order in which the active components are applied can be chosen at will.

The coated and dried and, if desired, calcined supports are subsequently activated by treatment in a gas stream comprising free hydrogen at from about 30 to about 600° C., preferably from about 150 to about 450° C. The gas stream preferably consists of from 50 to 100% by volume of $H_2$ and from 0 to 50% by volume of $N_2$.

The metal salt solution or solutions is/are applied to the support or supports in such an amount that the total active metal content, in each case based on the total weight of the catalyst, is from about 0.01 to about 30% by weight, preferably from about 0.01 to about 5% by weight, more preferably from about 0.01 to about 1% by weight and in particular from about 0.05 to about 1% by weight.

The total metal surface area on the catalyst 1 is preferably from about 0.01 to about 10 $m^2/g$, more preferably from about 0.05 to about 5 $m^2/g$ and in particular from about 0.05 to about 3 $m^2/g$, of the catalyst. The metal surface area is determined by means of the chemisorption method described by J. Lemaitre et al., in "Characterization of Heterogeneous Catalysts", edited by Francis Delanney, Marcel Dekker, New York 1984, pp. 310-324.

In the catalyst 1 used according to the present invention, the ratio of the surface area of the active metal/metals to that of the catalyst support is preferably less than about 0.05, with the upper limit being about 0.0005.

Support materials which can be used for producing the catalysts used according to the present invention are ones which are macroporous and have a mean pore diameter of at least about 50 nm, preferably at least about 100 nm, in particular at least about 500 nm, and whose surface area measured by the BET method is not more than about 30 $m^2/g$, preferably not more than about 15 $m^2/g$, more preferably not more than about 10 $m^2/g$, in particular not more than about 5 $m^2/g$ and much preferably not more than about 3 $m^2/g$. The mean pore diameter of the support is preferably from about 100 nm to about 200 µm, more preferably from about 500 nm to about 50 µm. The BET surface area of the support is preferably from about 0.2 to about 15 $m^2/g$, more preferably from about 0.5 to about 10 $m^2/g$, in particular from about 0.5 to about 5 $m^2/g$ and most preferably from about 0.5 to about 3 $m^2/g$.

The surface area of the support is determined by the BET method using $N_2$ adsorption, in particular in accordance with DIN 66131. The determination of the mean pore diameter and the pore size distribution is carried out by Hg porosimetry, in particular in accordance with DIN 66133.

The pore size distribution of the support can advantageously be approximately bimodal, with the pore diameter distribution having maxima at about 600 nm and about 20 µm in the bimodal distribution representing a preferred embodiment according to the invention.

Further preference is given to a support which has a surface area of 1.75 $m^2/g$ and displays this bimodal distribution of the pore diameter. The pore volume of this preferred support is preferably about 0.53 ml/g.

Macroporous support materials which can be used are, for example, macroporous activated carbon, silicon carbide, aluminum oxide, silicon dioxide, titanium dioxide, zirconium dioxide, magnesium oxide, zinc oxide and mixtures of two or more thereof, with preference being given to using aluminum oxide and zirconium dioxide.

Further details regarding catalyst 1 and its production may be found in DE-A 196 24 484.6, whose relevant contents are hereby fully incorporated by reference into the present patent application.

Support materials which can be used for producing the catalysts 1a used according to the present invention, which represent a preferred embodiment of catalyst 1, are ones which are macroporous and have a mean pore diameter of at least 0.1 µm, preferably at least 0.5 µm, and a surface area of not more than 15 m$^2$/g, preferably not more than 10 m$^2$/g, particularly preferably not more than 5 m$^2$/g, in particular not more than 3 m$^2$/g. The mean pore diameter of the support used there is preferably in a range from 0.1 to 200 µm, in particular from 0.5 to 50 µm. The surface area of the support is preferably from 0.2 to 15 m$^2$/g, particularly preferably from 0.5 to 10 m$^2$/g, in particular from 0.5 to 5 m$^2$/g, especially from 0.5 to 3 m$^2$/g of the support. This catalyst, too, has a bimodal pore diameter distribution analogous to that described above and the corresponding preferred pore volumes. Further details regarding catalyst 1a may be found in DE-A 196 04 791.9, whose relevant contents are fully incorporated by reference into the present patent application.

Catalyst 2

The catalysts 2 used according to the present invention comprise one or more metals of transition group VIII of the Periodic Table as active component(s) on a support.

The catalysts 2 used according to the present invention can be produced industrially by application of at least one active metal of transition group VIII of the Periodic Table, preferably ruthenium, and, if desired, at least one metal of transition group I, VII or VIII of the Periodic Table to a suitable support. Application to the support can be achieved by steeping the support in aqueous metal salt solutions, e.g. ruthenium salt solutions, by spraying appropriate metal salt solutions onto the support or by other suitable methods. Suitable metal salts for preparing the metal salt solutions are the nitrates, nitrosyl nitrates, halides, carbonates, carboxylates, acetylacetonates, chloro complexes, nitrito complexes or amine complexes of the corresponding metals, with preference being given to the nitrates and nitrosyl nitrates.

In the case of catalysts comprising a plurality of active metals applied to the support, the metal salts or metal salt solutions can be applied simultaneously or in succession.

The supports which have been coated or impregnated with the metal salt solution are subsequently dried, preferably at from 100 to 150° C. If desired, these supports can be calcined at from 200 to 600° C., preferably from 350 to 450° C. The coated supports are subsequently activated by treatment in a gas stream comprising free hydrogen at from 30 to 600° C., preferably from 100 to 450° C. and in particular from 100 to 300° C. The gas stream preferably consists of from 50 to 100% by volume of H$_2$ and from 0 to 50% by volume of N$_2$.

If a plurality of active metals are applied to the support and application is carried out in succession, the support can be dried at from 100 to 150° C. and, if desired, calcined at from 200 to 600° C. after each application or impregnation. In this case, the order in which the metal salt solutions are applied can be chosen at will.

The metal salt solution is applied to the support(s) in such an amount that the active metal content is from 0.01 to 30% by weight, preferably from 0.01 to 10% by weight, more preferably from 0.01 to 5% by weight and in particular from 0.3 to 1% by weight, based on the total weight of the catalyst.

The total metal surface area on the catalyst is preferably from 0.01 to 10 m$^2$/g, particularly preferably from 0.05 to 5 m$^2$/g and more preferably from 0.05 to 3 m$^2$/g, of the catalyst. The metal surface area is measured by the chemisorption method described in J. Lemaitre et al., "Characterization of Heterogenous Catalysts", edited by Francis Delanney, Marcel Dekker, New York (1984), pp. 310-324.

In the catalyst 2 used according to the present invention, the ratio of the surface area of the active metal(s) to that of the catalyst support is less than about 0.3, preferably less than about 0.1 and in particular about 0.05 or less, with the lower limit being about 0.0005.

Support materials which can be used for producing the catalysts 2 used according to the present invention contain macropores and mesopores.

The supports which can be used according to the present invention have a pore distribution in which from about 5 to about 50%, preferably from about 10 to about 45%, more preferably from about 10 to about 30% and in particular from about 15 to about 25%, of the pore volume is made up by macropores having pore diameters in the range from about 50 nm to about 10,000 nm and from about 50 to about 95%, preferably from about 55 to about 90%, more preferably from about 70 to about 90%, and in particular from about 75 to about 85%, of the pore volume is made up by mesopores having a pore diameter of from about 2 to about 50 nm, where the sum of the pore volumes is 100% in each case.

The total pore volume of the supports used according to the present invention is from about 0.05 to 1.5 cm$^3$/g, preferably from 0.1 to 1.2 cm$^3$/g and in particular from about 0.3 to 1.0 cm$^3$/g. The mean pore diameter of the supports used according to the present invention is from about 5 to 20 nm, preferably from about 8 to about 15 nm and in particular from about 9 to about 12 nm.

The surface area of the support is preferably from about 50 to about 500 m$^2$/g, more preferably from about 200 to about 350 m$^2$/g and in particular from about 250 to about 300 m$^2$/g, of the support.

The surface area of the support is determined by the BET method using N$_2$ adsorption, in particular in accordance with DIN 66131. The determination of the mean pore diameter and the size distribution is carried out by Hg porosimetry, in particular in accordance with DIN 66133.

Although it is in principle possible to use all support materials known in catalyst production, i.e. those which have the above-defined pore size distribution, preference is given to using activated carbon, silicon carbide, aluminum oxide, silicon dioxide, titanium dioxide, zirconium dioxide, magnesium oxide, zinc oxide or mixtures thereof, more preferably aluminum oxide and zirconium dioxide.

Further details regarding catalyst 2 may be found in DE-A 196 24 485.4, whose relevant contents are fully incorporated by reference into the present patent application.

According to the present invention, it is also possible to carry out the hydrogenation in the presence of a catalyst in a reaction column in which the reactants are passed over a catalyst fixed in the reaction column.

The present invention accordingly provides, in a further embodiment, a process for the hydrogenation of at least one substituted or unsubstituted, monocyclic or polycyclic aromatic in which the hydrogenation is carried out in a reaction column in which the reactants are passed over the catalyst fixed in the reaction column.

The reactants are preferably conveyed in countercurrent over the catalyst(s) fixed in the reaction column.

If the cycloaliphatics desired as product are taken on via a side offtake, the lower-boiling component (low boilers) are taken off at the top of the column. Correspondingly, the components having a boiling point higher than that of the cycloaliphatic (high boilers) are obtained at the bottom of the column. Accordingly, the mode of operation is matched to the by-products present in the aromatic(s) or formed during the reaction in each case. For example, low boilers are taken off at the top and high-boiling components are correspondingly taken off at the bottom, while the cycloaliphatic is obtained via a side offtake.

If no high-boiling by-products or secondary components are formed, the desired product is taken off at the bottom. Of course, it is also possible according to the present invention to employ a mode of operation in which the cycloaliphatics are obtained as desired products via the side offtake and at the bottom of the column.

Whether the cycloaliphatics are obtained at a side offtake or at the bottom of the column is controlled according to the present invention via the reflux ratio in the column and/or the energy input into the column. At the side offtake, the product is preferably taken off in liquid form.

In this embodiment, the catalytic hydrogenation is carried out in a reaction column over a heterogeneous catalyst which can in principle be any catalyst suitable for this application, in particular one of the catalysts 1, 1a and 2 described in detail above.

Furthermore, the following further heterogeneous catalysts comprising active metals can be used. As active metals, it is in principle possible to use all metals of transition group VIII of the Periodic Table. In this embodiment, preferred active metals are platinum, rhodium, palladium, cobalt, nickel or ruthenium or mixtures of two or more thereof, with particular preference being given to using ruthenium as active metal.

Among the metals of transition groups I and VII or else of I and VIII of the Periodic Table which can likewise all be used in principle, preference is given to using copper and/or rhenium.

Particular preference is given to using ruthenium alone. An advantage of the use of ruthenium as hydrogenation metal is that it enables considerable cost savings in catalyst production compared to the use of the significantly more expensive hydrogenation metals platinum, palladium and rhodium.

The ruthenium catalyst which is preferably used in the process of the present invention is placed in the column either in the form of a catalyst bed or as catalytically active distillation packing or as a combination of the two. The form of such a bed or distillation packing is known to those skilled in the art from the prior art.

Examples of metallic materials as support materials are pure metals such as iron, copper, nickel, silver, aluminum, zirconium, tantalum and titanium or alloys such as steels or stainless steels, e.g. steel comprising nickel, chromium and/or molybdenum. It is also possible to use brass, phosphor bronze, Monel metal and/or nickel silver or combinations of two or more of the abovementioned materials.

Examples of ceramic materials are aluminum oxide ($Al_2O_3$), silicon dioxide ($SiO_2$), zirconium oxide ($ZrO_2$), cordierite and/or steatite.

Examples of synthetic support materials are, for example, polymers such as polyamides, polyesters, polyethers, polyvinyls, polyolefins such as polyethylene, polypropylene, polytetrafluoroethylene, polyketones, polyether ketones, polyether sulfones, epoxy resins, aldehyde resins, urea-aldehyde and/or melamine-aldehyde resins. It is also possible to use carbon or glass fibers as supports.

Preference is given to using structured supports in the form of woven meshes, knitteds, foils or felts made of metal, woven meshes or felts, made of carbon fibers or woven meshes or knitteds made of polymer fibers. Possible woven wire meshes are woven meshes made of weavable metal wires such as iron, spring steel, brass, phosphor bronze, pure nickel, Monel metal, aluminum, silver, nickel silver, nickel, chromium-nickel, chromium steel, stainless, acid-resistant and high-temperature-resistant chromium-nickel steels and also titanium.

It is likewise possible to use woven meshes/fabrics made of inorganic materials, for example woven ceramic materials such as $Al_2O_3$ and/or $SiO_2$.

The structured supports or monoliths can consist of metallic, inorganic, organic or synthetic materials or combinations of such materials.

Wires and woven meshes/fabrics made of synthetic polymers can also be used in one embodiment of the invention.

Monoliths made of woven mesh packings are particularly preferred since they withstand high cross-sectional throughputs of gas and liquid and display only insignificant abrasion.

In a particularly preferred embodiment, use is made of metallic, structured supports or monoliths comprising stainless steel whose surface preferably undergoes roughening when heated in air and subsequently cooled. These properties are displayed by, in particular, stainless steels in which one alloy constituent accumulates at the surface above a specific demixing temperature and is oxidized in the presence of oxygen to form a firmly adhering, rough oxidic surface layer. Such an alloy constituent can be, for example, aluminum or chromium from which a surface layer of $Al_2O_3$ or $Cr_2O_3$ is formed. Examples of stainless steels are those having the material numbers 1.4767, 1.4401, 1.4301, 2.4610, 1.4765, 1.4847 and 1.4571. These steels can advantageously be thermally roughened by heating in air at from 400 to 1,100° C. for from 1 hour to 20 hours and subsequent cooling to room temperature.

In a preferred embodiment, the heterogenous catalyst is a ruthenium-coated woven mesh which simultaneously acts as distillation packing.

In a more preferred embodiment of the process of the present invention, the distillation packing consists of ruthenium-coated metal threads, particularly preferably of stainless steel having the number 1.4301 or 1.4767.

Further details regarding this embodiment, in particular regarding the production of the catalyst, are given in DE 100 50 711.5, whose relevant contents are fully incorporated by reference into the present patent application.

In a further embodiment, the present invention provides a process for the hydrogenation of a substituted or unsubstituted, monocyclic or polycyclic aromatic in which the catalyst comprises a metal of transition group VIII as active metal applied to a structured or monolithic support.

For the purposes of the present invention, structured supports are supports which have a regular two-dimensional or three-dimensional structure and are in this way distinguished from supports in particulate form which are used as a random bed. Examples of structured supports are supports made up of threads or wires, usually in the form of sheets such as woven meshes/fabrics, knitteds or felts. Structured supports can also include films or metal sheets which may also have holes, e.g. perforated metal sheets or expanded metal. For use in the process of the present invention, such essentially flat structured supports can be made into appropriately shaped three-dimensional structures, known as monoliths or monolithic supports, which can in turn be used, for example, as catalyst packing or column packing. Packings can also consist of a plurality of monoliths. It is likewise possible for the monoliths not to be fabricated from sheets of supports but instead to be produced directly without intermediate stages, for example the ceramic monoliths having flow channels which are known to those skilled in the art.

Before application of the active metals and any promoters, the structured or monolithic supports may, if appropriate, be coated with one, two or more oxides. This can be carried out by physical methods, for example by sputtering. Here, a thin layer of oxides, e.g. $Al_2O_3$, is applied to the support in an oxidizing atmosphere.

The structured supports can, for example, be shaped by means of a toothed roller and rolled up to produce a monolithic catalyst element either before or after application of the active metals and promoters.

The catalysts used for the purposes of the present invention may further comprise promoters as catalyst dopants, for example alkali metals and/or alkaline earth metals such as lithium, sodium, potassium, rubidium, cesium, magnesium, calcium, strontium and barium; silicon, carbon, titanium, zirconium, tungsten and the lanthanoids and actinoids; coinage metals such as copper, silver and/or gold, zinc, tin, bismuth, antimony, molybdenum, tungsten and/or other promoters such as sulfur and/or selenium.

The catalysts used according to the present invention can be produced industrially by application of at least one metal of transition group VIII of the Periodic Table and, if desired, at least one promoter to one of the above-described supports.

The application of the active metals and any promoters to the above-described supports can be carried out by vaporizing the active metals under reduced pressure and continuously condensing them on the support. Another possibility is to apply the active metals to the supports by treatment with solutions comprising the active metals and any promoters. A further possibility is to apply the active metals and any promoters to the supports by chemical methods such as chemical vapor deposition (CVD).

A further possibility is to treat the fixed supports, in particular meshes, woven fabrics and knitteds, with the impregnation solution in situ. Details regarding this method may be found in EP-A 0 803 488.

The catalysts produced in this way can be used directly or can be heat treated and/or calcined prior to use, and can be used either in a prereduced or unreduced state.

If desired, the support is pretreated before application of the active metals and any promoters. Pretreatment is advantageous when, for example, the adhesion of the active components to the support needs to be improved. Examples of pretreatments are coating the support with bonding agents and/or roughening by mechanical means (e.g. grinding, sand blasting) or thermal methods such as heat treatment, generally in air, or plasma etching.

The catalysts 3 and 4 which are preferably used will now be described below; with regard to general features of the catalysts 3 and 4, reference may be made to the above discussion.

Catalyst 3

The structured support or monolith used for catalyst 3 is preferably pretreated, for example by the above-described heating in air (thermal roughening) and subsequent cooling. The support is then preferably impregnated with a solution comprising the active metal (impregnation medium). If the support is an essentially flat structured support, this can be followed by fabrication into a monolithic catalyst element.

If the support is metallic, for example consists of stainless steel, it is preferably thermally roughened by heating in air at from 400 to 1,100° C. for from 1 hour to 20 hours and subsequent cooling to room temperature.

The impregnation of the support with the solution can be carried out by dipping the support into the solution, passing the solution over the support or spraying the solution onto the support.

The impregnation medium preferably has a surface tension of not more than 50 mN/m. In a more preferred embodiment, the impregnation medium has a surface tension of not more than 40 mN/m. The minimum value of the surface tension is generally subject to no restriction. However, the impregnation medium preferably has a surface tension of at least 10 mN/m, particularly preferably at least 25 mN/m. The surface tension is measured by the OECD ring method known to those skilled in the art (ISO 304, cf. EC Gazette No. L 383 of Dec. 29, 1992, pages A/47-A/53).

The impregnation medium preferably comprises a solvent or suspension medium, for example water, in which the active metals are dissolved, preferably in the form of their salts.

If desired, the impregnation medium can further comprise promoters for doping the catalyst. In this context, reference may be made to the above general discussion.

A solvent and/or suspension medium present in the impregnation medium is chosen so that the active components, active metals, promoters or precursors thereof to be applied undergo no undesirable reactions in it and/or with it.

Solvents and/or suspension media which can be used are the known and industrially customary solvents, for example aromatic or aliphatic hydrocarbons such as benzene, toluene, xylene, cumene, pentane, hexane, heptane, hydrocarbon fractions such as naphtha, ligroin, white oil, alcohols, diols, polyols, e.g. methanol, ethanol, the two propanol isomers, the four butanol isomers, glycol, glycerol, ethers such as diethyl ether, di-n-butyl ether, methyl tert-butyl ether, ethyl tert-butyl ether, methyl tert-amyl ether, ethyl tert-amyl ether, diphenyl ether, ethylene glycol dimethyl ether, diethylene glycol dimethyl ether, triethylene glycol dimethyl ether, or water. The organic solvents or suspension media used can also be substituted, for example by halogens, e.g. chlorobenzene, or by nitro groups, e.g. nitrobenzene. The solvents or suspension media are used individually or as mixtures.

The impregnation medium can further comprise, if necessary, auxiliaries. For example, the impregnation medium comprises acidic or basic compounds or buffers if this is necessary or advantageous for stabilizing or solubilizing at least one of its active components or precursors thereof.

Soluble salts of the active components are preferably dissolved completely in a solvent. An aqueous solution of active components is advantageously used.

If the active composition consists of metals, particular preference is given to using either an aqueous, nitric acid solution of the nitrates of the metals or an aqueous, ammoniacal solution of amine complexes of the metals. If the active components consist of amorphous metal oxides, preference is given to using an aqueous sol of the oxide, which may be stabilized.

The surface tension of the impregnation medium can be adjusted by means of suitable surface-active substances such as anionic or nonionic surfactants. The impregnated support is generally dried at from 100 to about 120° C. and, if appropriate, calcined at from 120 to 650° C., preferably from 120 to 400° C., after impregnation.

An essentially flat structured support can, after the thermal treatment, be fabricated into a three-dimensional structure having a shape appropriate to the purpose for which it is to be used. Shaping can be carried out, for example, by means of steps such as cutting to size, corrugating the sheets, arranging or fixing the corrugated sheets in the form of a monolith having parallel or crossed channels. Shaping to produce the monolith can be carried out either before impregnation, before drying, before thermal treatment or before chemical treatment.

Further details regarding catalyst 3 and its production may be found in DE-A 198 27 385.1, whose relevant contents are fully incorporated by reference into the present patent application.

Catalyst 4

The structured support or monolith used for catalyst 4 is preferably pretreated, for example by heating in air and subsequent cooling. The support is then preferably coated with at least one active metal under reduced pressure. If the support is an essentially flat structured support, it can subsequently be fabricated into a monolithic catalyst element.

Promoters as catalyst dopants are preferably also applied to the support material under reduced pressure in addition to the active metal/metals. Possible promoters have been described in the above general discussion.

The support material preferably consists of metal, particularly preferably stainless steel, more preferably stainless steels having the numbers mentioned above. The pretreatment of the support is preferably carried out by heating the metal support in air at from 600 to 1,100° C., preferably from 800 to 1,000° C., for from 1 to 20 hours, preferably from 1 to 10 hours. The support is subsequently cooled.

The active components (active metals and promoters) can be applied to the support by vapor deposition and sputtering. For this purpose, the support is coated discontinuously or continuously with the active components, either simultaneously or in succession, at a reduced pressure of from $10^{-3}$ to $10^{-8}$ mbar, preferably by means of a vaporization apparatus, e.g. electron beam vaporization, or sputtering apparatus. The catalyst can subsequently be activated by heating under inert gas or air.

The active components can be applied in a plurality of layers. The catalyst obtained in this way can then be fabricated into a monolith. In this respect, reference may be made to, inter alia, the details provided for catalyst 3. The catalyst is preferably fabricated by shaping (corrugating, creasing) the woven catalyst mesh or catalyst foil by means of a toothed roller and rolling up smooth and corrugated mesh to form a cylindrical monolith having similar vertical channels.

Further details regarding catalyst 4 and its production may be found in EP 0 564 830, whose relevant contents are fully incorporated by reference into the present patent application.

Catalyst 5

In a further preferred embodiment, the present invention relates to a process for the hydrogenation of at least one substituted or unsubstituted, monocyclic or polycyclic aromatic in which the catalyst comprises, as active metal, ruthenium alone or together with at least one further metal of transition group I, VII or VIII of the Periodic Table and is obtainable by:

i) single or multiple treatment of a support material based on amorphous silicon dioxide with a halogen-free aqueous solution of a low molecular weight ruthenium compound and a subsequent drying of the treated support material at a temperature below 200° C., ii) reduction of the solid obtained in i) by means of hydrogen at a temperature in the range from 100 to 350° C., where step ii) is carried out directly after step i).

Such catalysts (catalyst 5) have a particularly good distribution of ruthenium on the surface of the support material. As a result of the method of production, the ruthenium is present as metallic ruthenium in the catalysts used according to the present invention. The ruthenium is present on the support material in atomically dispersed form and/or in the form of ruthenium particles of which virtually all, i.e. more than 90%, preferably more than 95%, based on the number of visible particles, are isolated particles having diameters of less than 10 nm, in particular less than 7 nm. In other words, the catalyst contains essentially no, i.e. less than 10%, in particular less than 5%, of ruthenium particles or agglomerates of ruthenium particles having diameters above 10 nm. In addition, as a result of the use of halogen-free ruthenium precursors and solvents in the production of the catalyst, the chlorine content of the catalysts used according to the present invention is below 0.05% by weight, based on the total weight of the catalyst.

An important aspect of this catalyst (catalyst 5) is the use of a support material based on amorphous silicon dioxide. In this context, the term "amorphous" means that crystalline silicon dioxide phases make up less than 10% of the support material. The support materials used for producing the catalyst used according to the present invention may nevertheless have long-range structures formed by regular arrangement of pores in the support material.

Support materials which can be used are essentially all types of amorphous silicon dioxide which comprise at least 90% by weight of silicon dioxide, with the remaining 10% by weight, preferably not more than 5% by weight, of the support material being able to be another oxidic material, e.g. MgO, CaO, $TiO_2$, $ZrO_2$, $Fe_2O_3$ or an alkali metal oxide. It goes without saying that the support material used is likewise halogen-free, i.e. the halogen content is less than 500 ppm. The support material preferably contains not more than 1% by weight, in particular not more than 0.5% by weight and particularly preferably no detectable amounts, of aluminum oxide, calculated as $Al_2O_3$. In a preferred embodiment, support materials containing less than 500 ppm of $Fe_2O_3$ are used. The alkali metal oxide content generally results from the production of the support material and can be up to 2% by weight. It is frequently less than 1% by weight. Support materials which are free of alkali metal oxide (<0.1% by weight) are also suitable. The proportion of MgO, CaO, $TiO_2$ and $ZrO_2$ can be up to 10% by weight of the support material and is preferably not more than 5% by weight. However, support materials which contain no detectable amounts of these metal oxides (<0.1% by weight) are also suitable.

Preference is given to support materials which have a specific surface area in the range from 50 to 700 $m^2/g$, in particular in the range from 80 to 600 $m^2/g$ and especially in the range from 100 to 600 $m^2/g$ (BET surface area in accordance with DIN 66131). Pulverulent support materials preferably have a specific surface area in the range from 200 to 600 $m^2/g$, and shaped bodies preferably have a specific surface area in the range from 200 to 300 $m^2/g$.

Suitable amorphous support materials based on silicon dioxide are known to those skilled in the art and are commercially available (cf., for example, O. W. Flörke, "Silica" in Ullmann's Encyclopedia of Industrial Chemistry 5th ed. on CD-ROM). They can be of natural origin or can have been produced synthetically. Examples of suitable amorphous support materials based on silicon dioxide are Kieselguhr, silica gels, pyrogenic silica and precipitated silica. In a preferred embodiment of the invention, the catalysts comprise silica gels as support materials.

Depending on the way in which the hydrogenation process of the present invention is carried out, the support material can be in different forms. If the process is carried out as a suspension process, the support material is usually used in the form of a finely divided powder for producing the catalyst. When the catalyst is employed in a fixed bed, it is usual to use shaped bodies of support material which are obtainable, for example, by extrusion, ram extrusion or tabletting and can have the shape of spheres, pellets, cylinders, extrudates, rings or hollow cylinders, stars and the like. The dimensions of these shaped bodies are usually in the range from 1 mm to 25 mm. Use is frequently made of catalyst extrudates having diameters of from 2 to 5 mm and lengths of from 2 to 25 mm.

In a preferred embodiment, the present invention therefore provides a process for the hydrogenation of at least one substituted or unsubstituted, monocyclic or polycyclic aromatic in which the catalyst comprises less than 0.05% by weight of halogen, based on the total weight of the catalyst, and:

a support material based on amorphous silicon dioxide and elemental ruthenium either alone or together with at least one metal of transition group I, VII or VIII of the Periodic Table as metal which is present on the support in atomically dispersed form or in the form of metal particles or in atomically dispersed form and in the form of metal particles, where the catalyst contains essentially no metal particles or agglomerates having diameters above 10 nm.

In a more preferred embodiment, the present invention relates to a process in which the catalyst is regenerated.

Suitable methods of regenerating such a catalyst are, for example, treatment with halogen-free acid as described in U.S. Pat. No. 4,072,628, treatment with aqueous hydrogen peroxide or other halogen-free oxidizing substances or regeneration by means of oxygen as described in BE 882 279.

The catalyst 5 which can be used according to the present invention is described in more detail below:

The ruthenium content of the catalyst 5 can be varied over a wide range. In general, it will be at least 0.1% by weight, preferably at least 0.2% by weight, and frequently not exceed a value of 10% by weight, in each case based on the weight of the support material. The ruthenium content is preferably in the range from 0.2 to 7% by weight, in particular in the range from 0.4 to 5% by weight.

To produce the catalyst (5) used according to the present invention, the support material is firstly treated with a halogen-free aqueous solution of a low molecular weight ruthenium compound, hereinafter referred to as (ruthenium) precursor, in such a way that the desired amount of ruthenium is taken up by the support material. This step will hereinafter also be referred to as impregnation. The support which has been treated in this way is subsequently dried at the temperatures indicated above. If desired, the solid obtained in this way is again treated with the aqueous solution of the ruthenium precursor and dried again. This procedure is repeated until the amount of ruthenium compound taken up by the support material corresponds to the desired ruthenium content of the catalyst.

The treatment or impregnation of the support material can be carried out in various ways and depends in a known manner on the nature of the support material. For example, the support material can be sprayed with the precursor solution or the solution can be passed over the support material or the support material can be suspended in the precursor solution. For example, the support material can be suspended in the aqueous solution of the ruthenium precursor and can be filtered off from the aqueous solution after a certain time. The ruthenium content of the catalyst can then be controlled in a simple manner via the amount of liquid taken up and the ruthenium concentration of the solution. Impregnation of the support material can also be carried out, for example, by treating the support with a defined amount of the aqueous solution of the ruthenium precursor which corresponds to the maximum amount of liquid which can be taken up by the support material. For this purpose, the support material can, for example, be sprayed with the liquid. Suitable apparatuses for this purpose are those customarily used for mixing liquids and solids (cf., for example, Vauck, Müller "Grundoperationen chemischer Verfahrenstechnik", 10th edition, Deutscher Verlag für die Kunststoffindustrie, Leipzig, 1994, p. 405 ff.), for example tumble dryers, impregnation drums, drum mixers, blade mixers and the like. In the case of monolithic supports, the aqueous solutions of the ruthenium precursor are usually passed over/through the support.

The aqueous solutions used for impregnation are, according to the present invention, halogen-free, i.e. they contain no halogen or less than 500 ppm of halogen. The ruthenium precursors are therefore always ruthenium compounds which contain no chemically bound halogen and are sufficiently soluble in the aqueous solvent. These include, for example, ruthenium(III) nitrosyl nitrate ($Ru(NO)(NO_3)_3$), ruthenium(III) acetate and alkali metal ruthenates(IV) such as sodium or potassium ruthenate(IV).

In the present context, the term "aqueous" refers to water or mixtures of water with up to 50% by volume, preferably not more than 30% by volume and in particular not more than 10% by volume, of one or more water-miscible organic solvents, e.g. mixtures of water with $C_1$-$C_4$-alkanols such as methanol, ethanol, n-propanol or isopropanol. Water is frequently used as sole solvent. The aqueous solvent will frequently further comprise, for example, a halogen-free acid, e.g. a nitric acid, sulfuric acid or acetic acid, to stabilize the ruthenium precursor in the solution. The concentration of the ruthenium precursor in the aqueous solution naturally depends on the amount of ruthenium precursor to be applied and the uptake capacity of the support material for the aqueous solution and is generally in the range from 0.1 to 20% by weight.

Drying can be carried out by the customary methods of solids drying with adherence to the abovementioned temperatures. Adherence to the upper limit specified according to the present invention for the drying temperatures is important for the quality, i.e. the activity, of the catalyst. If the abovementioned drying temperatures are exceeded, this leads to a significant loss of activity. Calcination of the support at higher temperatures, e.g. above 300° C. or even 400° C., as proposed in the prior art, is not only superfluous but also has an adverse effect on the activity of the catalyst.

Drying of the solid impregnated with the ruthenium precursor is usually carried out under atmospheric pressure, but reduced pressure can also be employed to promote drying. A gas stream, e.g. air or nitrogen, is frequently passed over or through the material to be dried to promote drying.

The drying time naturally depends on the desired degree of drying and on the drying temperature and is generally in the range from 2 hours to 30 hours, preferably in the range from 4 to 15 hours.

The treated support material is preferably dried to such an extent that the content of water or of volatile solvent constituents prior to the reduction ii) is less than 5% by weight and in particular not more than 2% by weight, particularly preferably not more than 1% by weight, based on the total weight of the solid. The proportions by weight indicated refer to the weight loss of the solid determined at a temperature of 300° C., a pressure of 1 bar and a heating time of 10 min. The activity of the catalysts of the present invention can be increased further in this way.

Drying is preferably carried out with the solid treated with the precursor solution being kept in motion, for example by drying the solid in a rotary tube oven or a rotary sphere oven. The activity of the catalysts of the present invention can be increased further in this way.

The conversion of the solid obtained after drying into its catalytically active form is, according to the present invention, carried out by hydrogenation of the solid at the abovementioned temperatures in a manner known per se.

For this purpose, the support material is brought into contact with hydrogen or a mixture of hydrogen and an inert gas at the abovementioned temperatures. The hydrogen partial pressure is of minor importance for the result of the reaction and can be varied in a range from 0.2 bar to 1.5 bar. The hydrogenation of the catalyst material is frequently carried out in a stream of hydrogen under atmospheric pressure. Hydrogenation is preferably carried out with the solid obtained in i) being kept in motion, for example by hydrogenating the solid in a rotary tube oven or a rotary sphere oven. The activity of the catalysts of the present invention can be increased further in this way.

Subsequent to the hydrogenation, the catalyst can be passivated in a known manner, e.g. by briefly treating the catalyst with an oxygen-containing gas, e.g. air, but preferably an inert gas mixture containing from 1 to 10% by volume of oxygen, to improve handling.

Such catalysts are described in DE 101 282 42.7 or DE 101 282 05.2, whose relevant contents are fully incorporated by reference into the present patent application.

Further details of the process of the present invention are described below:

In the process of the present invention, it is in principle possible to use all substituted or unsubstituted, monocyclic or polycyclic aromatics either individually or as mixtures of two or more thereof, preferably individually.

If a substituted, monocyclic or polycyclicaromatic is used in the process of the present invention, the substituent may be inert in respect of hydrogenation. However, it is also possible according to the present invention for the aromatic to bear substituents having one or more hydrogenatable groups. Depending on the way the process is carried out, it is possible, according to the present invention, for only the aromatic or both the aromatic and the hydrogenatable group (s) to be hydrogenated. Hydrogenatable groups are, in particular, C—C, C—O, N—O or C—N multiple bonds. According to the present invention, it is possible, for example, to hydrogenate monocyclic or polycyclic aromatics which are substituted by one or more C—C double bonds or carbonyl groups.

The aromatic used in the process of the present invention can also bear one or more alkyl substituents. The length of the alkyl groups is subject to no particular restrictions, but the alkyl substituents are generally $C_1$-$C_{30}$-, preferably $C_1$-$C_{18}$-, in particular $C_1$-$C_4$-alkyl groups. Specific examples of starting materials which can be used in the present process are, in particular, the following aromatics:

Benzene, toluene, xylenes, cumene, diphenylmethane, tribebenzenes, tetrabenzenes, pentabenzenes and hexabenzenes, triphenylmethane, alkyl-substituted naphthalenes, naphthalene, alkyl-substituted anthracenes, anthracene, alkyl-substituted tetralins and tetralin.

According to the present invention, preference is given to hydrogenating unsubstituted or alkyl-substituted aromatics. Particular preference is given to hydrogenating benzene to cyclohexane in the present process.

However, starting materials which can be used according to the present invention also include, for example, heteroaromatics or aromatics in which at least one hydroxyl or amino group is bound to the aromatic ring.

For the purposes of the present invention, heteroaromatics are aromatic compounds containing at least one heteroatom, for example an N, S or O atom, in the aromatic ring.

If the monocyclic or polycyclic aromatic is substituted, it is possible for the cis/trans isomer ratio of the hydrogenation products to be varied within a wide range according to the present invention.

In the process of the present invention, the hydrogenation is generally carried out at from about 50 to 250° C., preferably from about 70 to 200° C., more preferably from about 80 to 180° C. and in particular from about 80 to 150° C. The lowest temperatures can be employed when ruthenium is used as active metal. The pressures used are generally above 1 bar, preferably from about 1 to about 200 bar, more preferably from about 10 to about 50 bar.

The process of the present invention can be carried out either continuously or batchwise, with preference being given to a continuous process.

In the continuous process variant, the amount of aromatic fed to the hydrogenation is from about 0.05 to about 3 kg per liter of catalyst per hour, more preferably from about 0.2 to about 2 kg per liter of catalyst per hour.

As hydrogenation gas, use is made of hydrogen in which residual gases are present. For the purposes of the present invention, the hydrogenation gas contains more than 75% of hydrogen based on the sum of hydrogen and residual gases, in particular more than 80%, particularly preferably more than 90%. According to the invention, it is possible to use, for example, hydrogen in which residual gases are present and which has been obtained in the dehydrogenation of ethylbenzene to styrene or of propane to propene.

According to the present invention, it is also possible for the hydrogen formed in the dehydrogenation reaction to be subjected to a purification step in which relatively high-boiling aromatic or aliphatic compounds or water or relatively high-boiling aromatic or aliphatic compounds and water are separated off. For the purposes of the present invention, "relatively high-boiling aromatic or aliphatic compounds" are compounds whose boiling point is above that of carbon monoxide and that of carbon dioxide. Carbon monoxide and carbon dioxide are not separated off in such a purification step.

The hydrogenation according to the present invention can be carried out in the absence or presence of a solvent or diluent, i.e. it is not necessary for the hydrogenation to be carried out in solution.

As solvent or diluent, it is possible to use any suitable solvent or diluent. The choice is not critical as long as the solvent or diluent used is able to form a homogeneous solution with the aromatic to be hydrogenated.

The amount of solvent or diluent used is not subject to any particular restrictions and can be chosen freely as required, but preference is given to amounts which lead to a 10-70% strength by weight solution of the aromatic to be hydrogenated.

When a solvent is used in the process of the present invention, the product formed in the hydrogenation, i.e. the respective cycloaliphatic(s), is used as solvent, if desired together with other solvents or diluents. In any case, part of the product formed in the process can be mixed into the aromatic which is yet to be hydrogenated. The amount of product mixed in as solvent or diluent is preferably from 1 to 30 times, particularly preferably from 5 to 20 times, and in particular from 5 to 10 times, the weight of the aromatic to be hydrogenated. In particular, the present invention provides a hydrogenation of the type under consideration in which benzene is hydrogenated at from 50 to 180° C. or from 80 to 180° C., preferably from 80 to 150° C., in particular from 100 to 120° C. or 110° C., in the presence of the catalyst 2 defined herein to form cyclohexane.

In a preferred embodiment, the invention provides a process for the hydrogenation of benzene in which benzene is reacted at from 80 to 180° C. and ruthenium alone is used as active metal.

The invention is illustrated by the following examples:

EXAMPLES

Example 1

Hydrogenation in the Liquid Phase

The dehydrogenation hydrogen from a styrene production plant which had a composition of 90.6% of $H_2$, 0.01% of $O_2$, 0.52% of $N_2$, 0.82% of methane, 0.18% of CO, 5.40% of $CO_2$, 0.22% of ethylene, 0.04% of ethane, 0.06% of propane, 0.14% of benzene, 343 ppm of toluene, 976 ppm of ethylbenzene and 625 ppm of styrene was compressed in two stages from about 1 bar to 20 bar and then used directly for the hydrogenation. 0.5 kg of ruthenium catalyst were placed in a tube reactor. The catalyst (0.5% of ruthenium on $Al_2O_3$ spheres) was produced as described in PCT/EP00/03326. Without prior activation, the hydrogenation of benzene was then commenced at 20 bar and 150° C. The hydrogenation was carried out continuously in the downflow mode with part of the output from the hydrogenation reactor being recirculated by means of a circulation pump admixed into the feed upstream of the reactor. The amount of hydrogenation product added as solvent in this way was 10 times the amount of benzene. The amount of benzene fed continuously to the reactor corresponded to a space velocity over the catalyst of 0.5 kg/(l*h).

The benzene was completely reacted in the hydrogenation. Cyclohexane was formed in a selectivity of 99.9%. Methylcyclopentane was not detected.

Example 2

Hydrogenation in the Gas Phase 100 ml of ruthenium catalyst were placed in an oil-heated flow-through reactor (glass). The catalyst (0.5% of ruthenium on $Al_2O_3$ spheres) was produced as described in PCT/EP00/03326. Without prior activation, hydrogenation of benzene was then commenced under atmospheric pressure. Benzene was vaporized in a prevaporizer (80° C.) and continuously passed together with hydrogen which had a composition of 90.6% of $H_2$, 0.01% of $O_2$, 0.52% of $N_2$, 0.82% of methane, 0.18% of CO, 5.40% of $CO_2$, 0.22% of ethylene, 0.04% of ethane, 0.06% of propane, 0.14% of benzene, 343 ppm of toluene, 976 ppm of ethylbenzene and 625 ppm of styrene and had been obtained directly from the synthesis of styrene in a single pass through the catalyst bed at 100° C. and a space velocity of 0.3 kg/(l*h). The output from the reactor was condensed in a cold trap.

In this way, benzene could be hydrogenated completely to cyclohexane. Cyclohexane was formed in a selectivity of 99.9%. Methylcyclopentane was not detected.

We claim:

1. A process for the hydrogenation of at least one substituted or unsubstituted, monocyclic or polycyclic aromatic, comprising bringing the aromatic or aromatics into contact with a hydrogenation gas in the presence of a catalyst which comprises at least one metal of transition group VIII of the Periodic Table as active metal, in an amount of from 0.01 to 30% by weight, based on the total weight of the catalyst, applied to a support, where from 10 to 50% of the pore volume of the support is made up by macropores having a pore diameter in the range from 50 nm to 10,000 nm and from 50 to 90% of the pore volume of the support is made up by mesopores having a pore diameter in the range from 2 to 50 nm, where the sum of the pore volumes is 100%, wherein the hydrogenation gas is obtained in the dehydrogenation of ethylbenzene to styrene or of propane to propene and wherein the hydrogenation gas comprises:
  from 50 to 98% by volume of $H_2$;
  less than 5% by volume of CO;
  from 0.01 to 15% by volume of $CO_2$;
  from 0 to 2% by volume of water;
  from 0 to 5% by volume of $N_2$; and
  from 0 to 5% by volume of other aromatics or aliphatic hydrocarbons.

2. A process as claimed in claim 1, wherein the hydrogenation gas comprises carbon monoxide, carbon dioxide, water, methane or C2-C7-hydrocarbons or mixtures of two or more thereof.

3. A process as claimed in claim 1, wherein the hydrogenation gas contains at least 2% by volume of residual gases selected from the group consisting of carbon monoxide, carbon dioxide, water, methane and C2-C7-hydrocarbons.

4. A process as claimed in claim 1, wherein the catalyst comprises at least one metal of transition group VIII of the Periodic Table as active metal applied to a macroporous support.

5. A process as claimed in claim 1, wherein the catalyst comprises at least one metal of transition group VIII of the Periodic Table as active metal applied to a structured or monolithic support.

6. A process as claimed in claim 1, wherein the hydrogenation is carried out in a reaction column wherein the aromatic or aromatics and the hydrogenation gas are passed over a catalyst fixed in the reaction column.

7. A process as claimed in claim 1, wherein the catalyst comprises, as active metal, ruthenium alone or together with at least one further metal of transition group I, VII or VIII of the Periodic Table and is obtainable by: i) single or multiple treatment of a support material based on amorphous silicon dioxide with a halogen-free aqueous solution of a low molecular weight ruthenium compound and a subsequent drying of the treated support material at a temperature below 200° C., ii) reduction of the solid obtained in i) by means of hydrogen at a temperature in the range from 100 to 350° C., where step ii) is carried out directly after step i).

8. A process as claimed in claim 7, wherein the catalyst comprises less than 0.05% by weight of halogen, based on the total weight of the catalyst, and: a support material based on amorphous silicon dioxide and elemental ruthenium either alone or together with at least one metal of transition group I, VII or VIII of the Periodic Table as metal which is present on the support in atomically dispersed form or in the form of metal particles or in atomically dispersed form and in the form of metal particles, where the catalyst contains essentially no metal particles or agglomerates having diameters above 10 nm.

9. A process as claimed in claim 1, wherein the monocyclic or polycyclic aromatic is selected from among benzene, toluene, xylenes, cumene, diphenylmethane, tribenzenes, tetrabenzenes, pentabenzenes and hexabenzenes, triphenylmethane, alkyl-substituted naphthalenes, naphthalene, alkyl-substituted anthracenes, anthracene, alkyl-substituted tetralins and tetralin.

10. A process as claimed in claim 1, wherein benzene is converted into cyclohexane.

11. A process as claimed in claim 1, wherein benzene is reacted at from 80 to 180 °C. and ruthenium alone is used as active metal.

* * * * *